United States Patent [19]

Tanaka et al.

[11] Patent Number: 5,057,533

[45] Date of Patent: Oct. 15, 1991

[54] AGRICULTURAL OR HORTICULTURAL FUNGICIDE

[75] Inventors: Kenichi Tanaka; Shinji Nishimura; Hiroshi Kawada; Katsuya Yamaguchi; Yumi Mizumura; Chieko Nomura, all of Tokyo, Japan

[73] Assignee: Hodogaya Chemical Co., Ltd., Tokyo, Japan

[21] Appl. No.: 557,810

[22] Filed: Jul. 26, 1990

[51] Int. Cl.$^5$ .................... C07D 233/56; A01N 43/50
[52] U.S. Cl. ........................................ 514/396; 548/335
[58] Field of Search .................. 548/335; 514/396

[56] References Cited

U.S. PATENT DOCUMENTS 4,720,549 1/1988 Zerbes et al. .................. 548/335

FOREIGN PATENT DOCUMENTS 62-187403 8/1987 Japan .
63-35564 2/1988 Japan .
63-154668 6/1988 Japan .

OTHER PUBLICATIONS

*Chemical Abstracts,* (1988), 109, p. 273, Abstract No. 144612t.

*Primary Examiner*—Mary C. Lee
*Assistant Examiner*—Lenora A. Miltenberger
*Attorney, Agent, or Firm*—Oblon, Spivak, McClelland, Maier & Neustadt

[57] ABSTRACT

An agricultural or horticultural fungicide comprising a compound of the following formula (I), as an active ingredient:

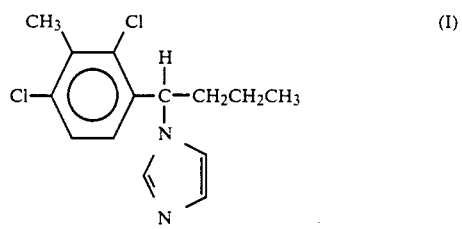

3 Claims, No Drawings

AGRICULTURAL OR HORTICULTURAL FUNGICIDE

The present invention relates to an agricultural or horticultural fungicide.

In modern agriculture, high productivity is secured by means of fertilizers, agricultural chemicals and various agricultural materials. On the other hand, emergence of chemical-resistant bacteria due to continuous application of agricultural chemicals and diseases due to repeated cultivation of the same crop plants in a locally concentrated fashion, have now become serious problems. Under these circumstances, it is strongly desired to develop highly safe agricultural and horticultural agents, and the present invention provides a means to meet such a desire.

The present invention provides an agricultural or horticultural fungicide comprising a compound of the following formula (I), as an active ingredient:

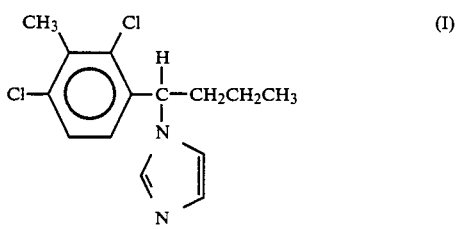

Now, the present invention will be described in further detail with reference to the preferred embodiments.

The compound of the formula (I) can be prepared by reacting a compound of the following formula (II) with imidazole in a suitable solvent.

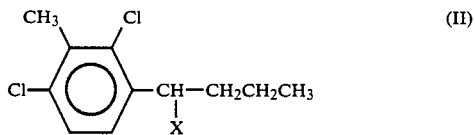

wherein X is a chlorine atom or a bromine atom.

The compound of the formula (II) can be prepared by a known reaction of the corresponding phenylalkylmethanol with e.g. thionyl chloride.

The main properties of the compound of the formula (I) are as follows:

Nature: oil
IR (cm$^{-1}$): 3098, 1584, 939, 912

For the application of the compound of the present invention, it may be formulated into a wettable powder, an emulsifiable concentrate, a granule, a dust, etc. by means of a solid carrier or a liquid carrier in accordance with a usual agricultural formulation method.

As the liquid diluent or carrier, an aromatic hydrocarbon such as xylene, a chlorinated aromatic hydrocarbon such as chlorobenzene, an alcohol such as butanol, a ketone such as methyl isobutyl ketone or isophorone, or a polar solvent such as dimethyl formamide or dimethyl sulfoxide, and water, are preferably employed.

As the solid diluent or carrier, a mineral powder such as kaolin, talc, clay, montmorillonite or diatomaceous earth, or a synthetic or natural polymer compound such as a polyalkylene glycol ester gum, may be employed.

Preferred emulsifiers include, for example, non-ionic emulsifiers such as polyoxyethylene fatty acid esters and polyoxyethylene alkylethers, and anionic emulsifiers such as alkylaryl sulfonates, aryl sulfonates and alkyl sulfonates. Preferred dispersants include, for example, lignin and methyl cellulose.

Extenders such as carboxymethyl cellulose as well as powdery, granular or grating natural and synthetic polymers such as gum Arabic, polyvinyl alcohol and polyvinyl acetate, may be used for the formulations.

The formulations usually contain from 0.1 to 95% by weight, preferably from 0.5 to 50% by weight, of the active compound.

The fungicide of the present invention is applied in a sufficient amount so that the active compound provides adequate effects. The dose of the active compound is within a range of from 50 to 2,000 g/ha, usually from 50 to 1,000 g/ha.

Now, the present invention will be described in further detail with reference to Examples. In these Examples, "parts" means "parts by weight".

EXAMPLE 1

| | |
|---|---|
| Compound of the formula (I) | 10 parts |
| Clay | 80 parts |
| Polyoxyalkylphenyl sulfate | 5 parts |
| White carbon (fine silica) | 5 parts |

The above materials were pulverized and mixed to obtain a wettable powder.

EXAMPLE 2

| | |
|---|---|
| Compound of the formula (I) | 20 parts |
| Xylene | 70 parts |
| Sorpol 800 A (trademark of Toho Chemical Co., Ltd. for a surfactant comprising a polyoxyethylene sorbitan alkylate, a polyoxyethylene alkylphenol polymer and calcium sulfonate, manufactured by Toho Chemical Co., Ltd.) | 10 parts |

The above materials were mixed to obtain an emulsifiable concentrate.

EXAMPLE 3

| | |
|---|---|
| Compound of the formula (I) | 10 parts |
| Lignin | 2 parts |
| Bentonite | 88 parts |

The above materials were mixed and kneaded with water, followed by granulation and drying to obtain a granule.

EXAMPLE 4

| | |
|---|---|
| Compound of the formula(I) | 20 parts |
| Isophorone | 10 parts |
| Xylene | 20 parts |
| Orthochlorotoluene | 35 parts |
| Sorpol 900 A (trade mark of Toho Chemical Co., Ltd. for a surfactant comprising a polyoxyethylene sorbitan alkylate, a polyoxyethylene alkylphenol polymer, a polyoxyethylene alkylallylether, and calcium sulfonate, manufactured by Toho Chemical Co., Ltd.) | 7.5 parts |
| Sorpol 900 B (trade mark of Toho Chemical Co., Ltd. for a surfactant comprising a polyoxyethylene sorbitan alkylate, a polyoxyethylene alkylphenol | 7.5 parts |

-continued polymer, a polyoxyethylene alkylallylether, and calcium sulfonate, manufactured by Toho Chemical Co., Ltd.)

The above materials were mixed to obtain an emulsifiable concentrate.

Now, mycelium growth inhibitory effects and disease protectant activity of the compounds of the present invention against typical fungi will be described with respect to Test Examples.

TEST EXAMPLE 1

Test for mycelium growth inhibitory effects on a Petri dish

A potato-dextrose agar culture medium (PDA medium) and a dimethyl sulfoxide solution of the compound were mixed to a concentration of 100 ppm, and the mixture was poured into a Petri dish to form a plate culture medium. Onto this culture medium, two disc specimens with a diameter of 4 mm of each of *Pythium graminicola*, *Fusarium oxysporum* and *Rhizoctonia solani*, which were preliminarily cultured on PDA culture media, were placed, and cultured at 25° C. for two days in the case of *Pythium graminicola*, five days in the case of *Fusarium oxysporum* and for three days in the case of *Rhizoctonia solani*. Then, the diameter of each colony was measured and compared with the colony diameter on a non-treated medium, and the growth inhibition was calculated in accordance with the following equation.

$$\text{Growth inhibition (\%)} = \frac{A - B}{A} \times 100$$

A: Colony diameter on the non-treated medium
B: Colony diameter on the treated medium The average values of the results are shown in Table 1.

TABLE 1

| Fungi | Pythium graminicola | Fusarium oxysporum | Rhizoctania solani |
|---|---|---|---|
| Growth inhibition by Compound of the formula (I) | 100 | 100 | 100 |

TEST EXAMPLE 2

Test for protectant activity against downy mildew of cucumber

Cucumber (variety: Kashu No. 1) was cultured in a porous porcelain pot having a diameter of 9 cm, and when it reached a 3-leaf stage, the wettable powder of the test compound formulated in accordance with Example 1 was diluted to have a concentration of 100 ppm, and 20 ml of the solution of the test compound was sprayed by means of a spray gun. Three cucumber plants were treated with each test compound.

After drying them 24 hours, a suspension of spores $(2 \times 10^5$ spores/ml) of *Pseudoperonosporea cubensis* causing downy mildew of cucumber, was sprayed and inoculated to each plant. After the inoculation, the cucumber plants were cultured at 20° C. under a moisture-saturated condition for 12 hours and then at 20° C. under a relative humidity of from 70 to 80% for 6 days. Seven days after the inoculation, the proportions of lesion on the first leaf and the second leaf were examined, and the control value were determined by the following formula to obtain the results as shown in Table 2. As a comparative compound, Compound A as identified in Table 3 was used.

$$\text{Control value} = \frac{C - D}{C} \times 100$$

C: Proportion of lesion at the non-treated section
D: Proportion of lesion at the treated section

TABLE 2

| Compound | Control value |
|---|---|
| I | 80 |
| A | 0 |

TABLE 3

| Symbols for comparative compounds | Structures of comparative compounds | Common names |
|---|---|---|
| A | $CH_3$, Cl, Cl—phenyl—CH—CH$_3$, N, imidazole | |
| B | $CH_3$, Cl, Cl—phenyl—CH-nC$_6$H$_{13}$, N, imidazole | |
| C | $CH_2$, Cl, Cl—phenyl—CH-isoC$_4$H$_9$, N, imidazole | |
| D | Cl, Cl—phenyl—C(O—CH$_2$—CH(nC$_3$H$_7$)—O), CH$_2$—N—triazole | Propiconazole |

TEST EXAMPLE 3

Test for protectant activity against powdery mildew of wheat

Wheat (variety: Norin No. 61) was cultured in a pot having a diameter of 9 cm, and when it reached a 2-leaf stage, the emulsifiable concentrate of the test compound formulated in accordance with Example 4 was diluted to have a concentration of 100 ppm, and 20 ml of the solution of the test compound was sprayed by means of a spray gun. With respect to each test compound, treatment was conducted in two series each consisting of 13 wheat plants per section.

After drying the plants for 24 hours, conidia of *Eryshiphe graminis* causing powdery mildew of wheat, were sprayed and inoculated to each wheat plant. After this inoculation, the wheat plants were cultured at 20° C. in a dark place under a moisture-saturated condition for 12 hours and then at 20° C. for 6 days. Seven days after inoculation, the portions of lesion on the first leaf and the second leaf were examined, and the control value was obtained in the same manner as in Test Example 2 to obtain the results as shown in Table 4. As a comparative compound, Compound B as identified in Table 3 was used.

TABLE 4

| Compound | Control value |
| --- | --- |
| I | 100 |
| B | 10 |

TEST EXAMPLE 4

Test for protectant activity against glume-blotch of wheat

Wheat (variety: Norin No. 61) was cultured in a pot having a diameter of 9 cm, and when it reached a 2-leaf stage, the emulsifiable concentrate of the test compound formulated in accordance with Example 4 was diluted to have a concentration of 100 ppm, and 20 ml of the solution of the test compound was sprayed by means of a spray gun. With respect to each test compound, treatment was conducted in two series each consisting of 13 wheat plants per section.

After drying the plants for 24 hours, a suspension of spores ($10^6$ spores/ml) of *Lepto-sphaeria nodorum* causing glume-blotch of wheat, was sprayed and inoculated to each wheat plant. After this inoculation, the wheat plants were cultured at 18° C. under a relative humidity of 90% for 10 days. 10 days after the inoculation, the proportions of lesion on the first leaf and the second leaf were examined, and the control value was obtained in the same manner as in Test Example 2 to obtain the results as shown in Table 5. As a comparative compound, Compound C as identified in Table 3 was used.

TABLE 5

| Compound | Control value |
| --- | --- |
| I | 100 |
| C | 40 |

TEST EXAMPLE 5

Test for eradicant effects against powdery mildew of wheat

Wheat (variety: Norin No. 61) was cultured in a pot having a diameter of 9 cm, and when it reached a 2-leaf stage, conidia of *Eryshiphe graminis* causing powdery mildew of wheat were sprayed and inoculated. After this inoculation, the wheat plants were cultured at 20° C. in a dark place under a moisture-saturated condition for 12 hours. Then, the emulsifiable concentrate of the test compound formulated in accordance with Example 4 was diluted to have a concentration of 1 ppm, and 20 ml of this solution was sprayed by means of a spray gun. With respect to each test compound, treatment was conducted in two series each consisting of 13 wheat plants per section.

After the application of the compound, the plants were cultured at 20° C. for 6 days. Seven days after the inoculation, the portions of lesion on the first leaf and the second leaf were examined, and the control value was obtained in the same manner as in Test Example 2 to obtain the results as shown in Table 6. As a comparative compound, Compound D as identified in Table 3 was used.

TABLE 6

| Compound | Control value |
| --- | --- |
| I | 100 |
| D | 40 |

As described in the foregoing, the present invention exhibits fungicidal activities against various filamental fungi and shows protectant activity against diseases of crop plants, and thus it presents an effective means for improving the yield of harvest without phytotoxicity.

We claim:

1. An agricultural or horticultural fungicide comprising a compound of the following formula (I) as an active ingredient:

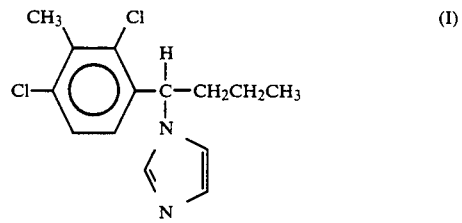

and an agriculturally or horticulturally acceptable carrier.

2. The compound having the formula (I) shown below

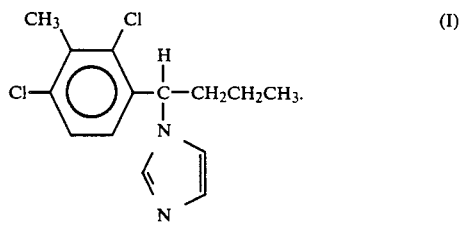

3. A method of inhibiting agricultural and horticultural fungi, comprising contacting agricultural or horticultural fungi with an inhibitory amount of the compound having the formula (I)
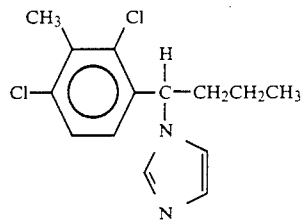
or an agricultural or horticultural composition containing said compound.